(12) United States Patent
Lefebvre et al.

(10) Patent No.: US 11,906,459 B2
(45) Date of Patent: Feb. 20, 2024

(54) SENSOR PLATFORM

(71) Applicant: National Research Council of Canada, Ottawa (CA)

(72) Inventors: Jacques Lefebvre, Stoneham-et-Tewkesbury (CA); François Lapointe, Gatineau (CA)

(*) Notice: Subject to any disclaimer, the term of this patent is extended or adjusted under 35 U.S.C. 154(b) by 447 days.

(21) Appl. No.: 17/292,844

(22) PCT Filed: Aug. 16, 2019

(86) PCT No.: PCT/CA2019/051116
§ 371 (c)(1),
(2) Date: May 11, 2021

(87) PCT Pub. No.: WO2020/102880
PCT Pub. Date: May 28, 2020

(65) Prior Publication Data
US 2021/0293737 A1 Sep. 23, 2021

Related U.S. Application Data

(60) Provisional application No. 62/769,621, filed on Nov. 20, 2018.

(51) Int. Cl.
| | | |
|---|---|---|
| *G01N 27/22* | (2006.01) | |
| *G01N 27/12* | (2006.01) | |
| *G01N 27/414* | (2006.01) | |

(52) U.S. Cl.
CPC ......... *G01N 27/225* (2013.01); *G01N 27/121* (2013.01); *G01N 27/4141* (2013.01); *G01N 27/4146* (2013.01)

(58) Field of Classification Search
CPC .............. G01N 27/225; G01N 27/121; G01N 27/4141; G01N 27/4146; G01N 27/126;
(Continued)

(56) References Cited

U.S. PATENT DOCUMENTS

| | | |
|---|---|---|
| 3,831,432 A | 8/1974 | Cox |
| 4,542,640 A | 9/1985 | Clifford |

(Continued)

FOREIGN PATENT DOCUMENTS

| | | |
|---|---|---|
| DE | 10 2011 002 854 A1 | 2/2012 |
| EP | 2239561 A1 | 10/2010 |

(Continued)

OTHER PUBLICATIONS

Office action dated Feb. 24, 2023 on Taiwan application 108129502.
(Continued)

*Primary Examiner* — Giovanni Astacio-Oquendo
(74) *Attorney, Agent, or Firm* — Brunet & Co. Ltd.; Hans Koenig; Robert Brunet

(57) ABSTRACT

An electronic device for sensing a target analyte in a gas, liquid or vapor sample, the device has at least two sensing elements, each sensing element having an exposed layer of a transduction material supported on a dielectric substrate. The dielectric substrate of at least one of the sensing elements is made of a different dielectric material than the dielectric substrate of at least one other of the sensing elements. The different dielectric materials providing a different sensing response according to one or more transduction modes. The plurality of sensing elements in the device yield a specific transduction pattern for a specific target analyte in a gas, liquid or vapor sample.

20 Claims, 10 Drawing Sheets

(58) Field of Classification Search
CPC .. G01N 27/127; G01N 27/129; G01N 27/221; G01N 33/0036; G01N 33/0031; G01N 27/27
USPC ............... 324/686, 658, 649, 600
See application file for complete search history.

(56) References Cited

U.S. PATENT DOCUMENTS

| | | | |
|---|---|---|---|
| 5,571,401 | A | 11/1996 | Lewis et al. |
| 5,844,486 | A | 12/1998 | Kithil et al. |
| 6,528,020 | B1 | 3/2003 | Dai et al. |
| 6,773,926 | B1 | 8/2004 | Freund et al. |
| 6,905,655 | B2 | 6/2005 | Gabriel et al. |
| 8,344,739 | B2 | 1/2013 | Van Gastel et al. |
| 2005/0221473 | A1 | 10/2005 | Dubin et al. |
| 2006/0263255 | A1 | 11/2006 | Han et al. |
| 2010/0323925 | A1 | 12/2010 | Gabriel et al. |
| 2013/0075794 | A1 | 3/2013 | Bradley et al. |
| 2016/0003770 | A1 | 1/2016 | Klootwijk et al. |
| 2018/0266977 | A1* | 9/2018 | Hashizume .......... G01N 29/036 |
| 2020/0400604 | A1* | 12/2020 | Jung .................. G01N 27/129 |
| 2022/0276192 | A1* | 9/2022 | Akimoto ............. G01N 27/226 |

FOREIGN PATENT DOCUMENTS

| | | |
|---|---|---|
| JP | 2009150714 A | 7/2009 |
| RU | 2010154802 A | 7/2012 |
| RU | 2586284 C1 | 6/2016 |
| RU | 2614667 C1 | 3/2017 |
| RU | 2619261 C1 | 5/2017 |

OTHER PUBLICATIONS

Zhang T, et al. "Recent progress in carbon nanotube-based gas sensors," Nanotechnology, vol. 19, 332001, Jul. 7, 2008.
Zhang X, et al. "Sorting semiconducting single walled carbon nanotubes by poly(9,9-dioctylfluorene) derivatives and application for ammonia gas sensing," Carbon,vol. 94, pp. 903-910, Jul. 23, 2015.
Office action dated Aug. 7, 2023 on Taiwan application 108129502.
Extended European Search Report dated Jun. 20, 2022 on European application 19887043.8.
Lapointe Frangois et al: "Carbon Nanotube Transistors as Gas Sensors: Response Differentiation Using Polymer Gate Dielectric"; ACS Applied Polymer Materials; vol. 1, No. 12, Dec. 11, 2019, pp. 3269-3278.
P. Bondavalli et al: "Gas fingerprinting using carbon nanotubes transistor arrays", Journal of Experimental Nanoscience, vol. 3, No. 4, Jan. 12, 2008, pp. 347-356.
International Search Report and Written Opinion dated Oct. 11, 2019 on PCT/CA2019/051116.
Lee CY, et al. Angew. Chem. Int. Ed. 2008, 47, 5018-5021.
Lipatov A, et al. Nanoscale, 2013, 5, 5426.
Lu Y, et al. Journal of Electroanalytical Chemistry 593 (2006) 105-110.
Moreno L, et al. Sensors and Actuators B 116 (2006) 130-134.
Pei H, et al. J. Am. Chem. Soc. 2012, 134, 13843-13849.
Qi P, et al. Nano Letters (2003) vol. 3, No. 3, 347-351.
Some S, et al. Scientific Reports (2103) 3 : 1868 | DOI: 10.1038/srep01868.
Star A, et al. J. Phys. Chem. B 2006, 110, 21014-21020.
Tomchenko A, et al. Sensors and Actuators B 93 (2003) 126-134.
Office action dated Jun. 22, 2023 on Japanese patent application JP 2021-527851.

* cited by examiner

| | VC / Polymer | H₂O | H₂O₂ | Vinegar | NaOCl | Acetone | Tetrahydrofuran | Methanol | Isopropanol | Toluene | n-Octane | Heptane | IsoButylAmine | dIsoButylAmine | TriEthylAmine | TriPropylAmine | AdMPyrazine |
|---|---|---|---|---|---|---|---|---|---|---|---|---|---|---|---|---|---|
| Lagging | SiO₂ | | | | | | | | | | | | | | | R | |
| Lagging | MXD6 | | | | | | | | | | | | | | | R | |
| Lagging | P4VP | | | | • | | • | • | | | • | • | • | | | • | R | • |
| Lagging | P4VP-PS10 | | | | | | | | | | | | | | | R | |
| Free | Merck D139 | | | | | | | | | | | | | | | R | |
| Free | Teflon™ AF | • | • | • | • | | • | | | | • | • | • | | | • | R | • |
| Free | Parylene C | | | | | | | | | | | | | | | R | |
| Free | Parylene HT | • | | | • | | • | | | | • | • | • | | | • | R | • |
| Free | PVP-pMSSQ | | | | • | | | | | | | | | | | R | |
| Free | PA6(3)T | | | | • | • | • | | | | • | | • | • | • | R | |
| Free | PA10T | | | | | | | | | | | | | | | R | |
| Free | Cellulose Nitrate | | | | | | | | | | | | | | | R | |
| Advancing | Cellulose Acetate | | | | | | | | | | | | | | | R | |
| Advancing | Cyano Ethyl Cellulose | | | | | | | | | | | | | | | R | |
| Advancing | Nylon 66 | | • | | • | | • | | | | • | • | • | | | • | R | • |
| Advancing | Nylon 610 | | | | | | | | | | | | | | | R | |
| Advancing | Nylon 612 | | | | | | | | | | | | | | | R | |
| Advancing | Nylon 12 | | • | | • | | • | | | | • | • | • | | | • | R | • |
| Advancing | PVDF | | | | | | | | | | | | | | | • | R | |

Fig. 11

SENSOR PLATFORM

CROSS-REFERENCE TO RELATED APPLICATIONS

This application is a national entry of PCT/CA2019/051116 filed Aug. 16, 2019 and claims the benefit of United States Provisional patent application U.S. Ser. No. 62/769,621 filed Nov. 20, 2018, the entire contents of both of which are herein incorporated by reference.

FIELD

This application relates to electronic sensors, in particular to electronic sensors for detecting at least one target analyte from a gas, liquid or vapor.

BACKGROUND

CNT sensors, especially those based on semiconducting single-walled carbon nanotubes (sc-SWCNTs), offer many desirable features for a new generation of broadly deployable, high performance and printed low-cost electronic devices to be implemented in internet of things and wearable devices. CNT sensors based mainly but not exclusively on electronic transduction (e.g. chemiresistor, capacitive, transistor) are very sensitive due to the large surface area offered by the CNT material. Selectivity to specific analytes (e.g. gases or solvated molecules), however, is generally very poor due to limited reactivity of the nanotube sidewall. Further, current sensor architectures present little or no control over the interface surrounding the nanotubes.

Improving selectivity of CNT-based sensors to given analytes may be achieved by a number of different methods including: coating CNTs with chemically different films; covalent or non-covalent chemical functionalization of CNTs; decoration of the CNTs sidewalls with nanoparticles; combining CNTs with another transduction material; and, chemical functionalization of the substrate or contact electrodes. Each method has specific attributes and can be used for a target sensing application. Common to these sensors is that the underlying substrate has no function other than mechanical support. However, for single-walled CNTs, all nanotube atoms are exposed to the interface between the environment and the substrate. The interface thus plays an important role in performance, and significant interference can arise from surrounding materials, especially for thin film transistors. Such interference currently constitutes a serious limitation for CNT-based sensing. For example, the substrate interface presents surface states, dipoles and charge traps, and therefore plays an important role in device performance, operation variability and sensor response. In a transistor where the channel and dielectric interface are left unprotected, several if not all transistor metrics become sensitive to fluctuations in ambient conditions. The best-known example is the hydrophilic $SiO_2$ dielectric where bare transistors in bottom gate configuration are unipolar p-type in air ambient with significant hysteresis between forward and reverse gate sweep directions. The effect of the $O_2/H_2O$ redox process was demonstrated to be the dominant mechanism responsible for suppression of n-type conduction. On such transistors, day-to-day variations of transistor parameters are observed upon changes in air ambient conditions. For several electronics applications, this is not acceptable and proper encapsulation is required. However, from a sensing perspective, this attribute is quite appealing provided some degree of control can be achieved. Substrate-induced variability may be used advantageously, if the variability can be rationalized and controlled. Despite the recognized role of the substrate role on transistor performance, the importance of the substrate on the sensing response has been overlooked and most studies have focused on inorganic dielectrics, mainly $SiO_2$.

There remains a need for sensors, especially CNT-based sensors, based on orthogonal signals and data analysis.

SUMMARY

In one aspect, there is provided an electronic device for sensing a target analyte in a gas, liquid or vapor sample, the device comprising at least two sensing elements, each sensing element comprising an exposed layer of a transduction material supported on a dielectric substrate, wherein the dielectric substrate of at least one of the sensing elements comprises a different dielectric material than the dielectric substrate of at least one other of the sensing elements, the different dielectric materials providing a different sensing response according to one or more transduction modes.

There is further provided a process for sensing a target analyte in a gas, liquid or vapor sample, the process comprising: exposing the device as defined above to a gas, liquid or vapor sample containing a target analyte; and, measuring a different sensing response between the at least two sensing elements according to one or more transduction modes.

The sensing elements may be resistors (e.g. chemiresistors), capacitors, diodes, transistors, electrochemical cells, or combinations thereof. Electronic sensing devices operate according to four transduction modes. The analyte may cause: 1) a shift of the Fermi level of the sensing element (electrostatic; chemical doping); 2) a modulation of the Schottky barrier of the sensing element (charge carrier injection efficiency; contact resistance); 3) a change in the dielectric environment around the sensing element (effective dielectric constant; gate capacitance); and/or, 4) a change in the charge carrier diffusivity of the sensing element (charge carrier mobility; channel resistance). The major effect of the substrate dielectric on the electronic properties of the sensing element occurs through 1) shift of the Fermi level and 3) change in the dielectric environment. Moreover, interchanging the substrate dielectric also offers the opportunity to change the interaction strength of the analyte with the substrate because of the change in the chemical nature of the interface. This results in more or less affinity for certain types of molecules. The combination of transduction materials and dielectric materials yields different transduction patterns of the sensing elements for different target analytes. The transduction signal of a given sensing element is thus a convolution of a) the effect of the substrate dielectric on the electronic properties of the sensing element, b) the effect of the substrate dielectric on the analyte's specific interaction strength with the device, and c) the effect of the analyte on the device through transduction modes 1) to 4).

Therefore, the underlying dielectric interface can be utilized to tune the electronic properties of the sensing element in a way that favors predominantly one of the four transduction modes. Because dielectric substrates behave slightly differently in the sensing device with respect to each of the transduction modes for a given analyte or set of analytes, an individual sensing element may not be specific to a particular target analyte but a sensing device comprising several elements can recognize the target analyte according to the transduction patterns from multiple signals. A sensing device that comprises sensing elements having different dielectric substrates can therefore have markedly improved selectivity for not just one target analyte but for target analytes in a set of target analytes.

Thus, the device may utilize a back gate dielectric sensing mode in which a proximal surface of the dielectric substrate (i.e. a surface of the dielectric substrate on which the transduction material is supported) becomes the dominant vector of analyte interaction while the transduction material provides the necessary electrical transduction. In this sensing mode, the choice of dielectric material (organic and/or inorganic) modulates sensor response even if a single source of pristine or functionalized transduction material is used. This strategy lends itself well to a printable electronic nose built from an array of dielectric substrates, especially dielectric substrates comprising organic polymer.

Various combinations of sensing element in the sensing device are possible. For example, the dielectric substrates of every one of the sensing elements may comprise different dielectric materials, the dielectric substrates of at least two of the sensing elements may comprise the same dielectric material, at least two of the two dielectric materials may have different interaction strengths with the target analyte, or at least one of the dielectric materials may have an effect on transduction in the device of a nature different than the nature of the effect on transduction of another of the dielectric materials. Other combinations are possible.

The dielectric substrate material provides an additional degree of freedom in the implementation of cross-reactive chemical sensor arrays to move past the "lock-and-key" traditional detection scheme. An extensive survey of polymeric materials as described herein has led to markedly different signatures to humidity and volatile compounds in terms of threshold voltage, hysteresis and transconductance, demonstrating the power of using a rich set of transistor metrics in sensing applications. A printed electronic nose may thus comprise carbon nanotube transistor sensing elements with gate dielectrics substrate materials comprising various polymers. By leveraging the sensing responses' orthogonality, an improved performance in molecular recognition is achieved, especially in combination with advanced data analytics.

Further features will be described or will become apparent in the course of the following detailed description. It should be understood that each feature described herein may be utilized in any combination with any one or more of the other described features, and that each feature does not necessarily rely on the presence of another feature except where evident to one of skill in the art.

BRIEF DESCRIPTION OF THE DRAWINGS

For clearer understanding, preferred embodiments will now be described in detail by way of example, with reference to the accompanying drawings, in which:

FIG. 5(b) and FIG. 5(c) show RH dependence of transistor threshold voltage and transconductance. Data from multiple humidity cycles between 10 and 60% are shown.

FIG. 6(b) and FIG. 6(c) show RH dependence of transistor threshold voltage and transconductance for the three polymers in FIG. 6(a).

FIG. 9(a) shows transfer characteristics for three polymer dielectrics, PVP-pMSSQ, PA66, and Merck D139 compared to $SiO_2$ with arrows indicating gate sweep direction and black lines are linear fits extracted from a section of the transfer characteristics indicated in bold gray. FIG. 9(b) shows time dependence of transistor threshold voltage and transconductance upon exposure to eight volatile compounds (methanol (MeOH), water ($H_2O$), vinegar, isopropylamine (IPA), acetone, tripropylamine (TPA), and diisobutylamine (dIBA). Parameters are extracted from the linear fit as illustrated in FIG. 9(a). One data point was acquired every 7 s.

FIG. 11 depicts a table summarizing compounded transistor response on exposure to volatile compounds. Data is presented in three color intensities from white (significantly lower) to dark (significantly higher) based on the response compared to tripropylamine (R). Dotted squares have not been measured. Dielectric materials are grouped according to hysteresis in ambient air: lagging, free and advancing.

DETAILED DESCRIPTION

Figure 1:
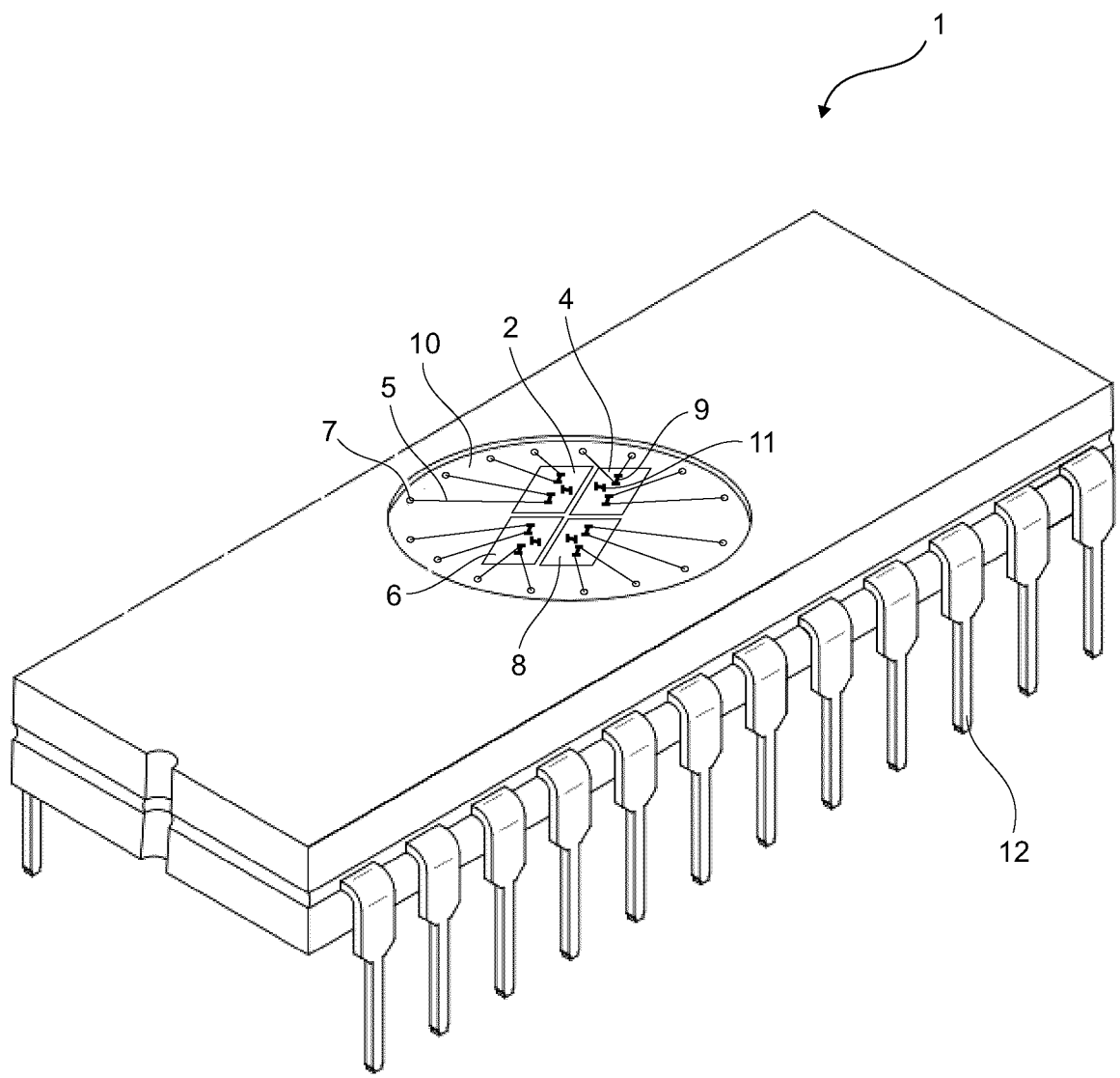
FIG. 1 depicts a sensing device for analyte detection using an array of sensor elements having substrates made from different dielectric materials.

The sensing device comprises an array of sensing elements, where at least one of the sensing elements comprises a dielectric substrate comprising a dielectric material that provides a different sensing response according to one or more transduction modes. The dielectric material may have a different effect on how the target analyte shifts the Fermi level of the sensing element, a different effect on how the target analyte changes the dielectric environment of the sensing element, a different effect on how the target analyte modulates the Schottky barrier of the sensing element and/or a different effect on how the target analyte changes the charge carrier diffusivity of the sensing element. The dielectric material may have a different interaction strength with the target analyte compared to a dielectric material of at least one dielectric substrate in another of the sensing elements. In this manner, the substrates themselves contribute to the sensing function.

The dielectric material may be organic, inorganic or an organic/inorganic hybrid. Preferably, the dielectric material comprises a polymer. In one embodiment, the dielectric material comprises an organic polymer. Some examples of dielectric materials are silicon dioxide, silicon nitride, alumina, polyamides, polyvinylphenols, polysilsesquioxanes, polyacrylates, polyfluorinated alkanes, polystyrenes, polyvinylpyridines, cellulose derivatives, poly(p-xylylenes), copolymers thereof, blends thereof or hybrids thereof.

The transduction material is formed on the dielectric substrate as a layer that is exposed to the target analyte when the device is exposed to the sample. The transduction material may be in the form of polymers, non-polymeric molecules, nanowires, nanorods, nanotubes, nanoparticles or any combination thereof. In some embodiments, the transduction material may be permeable to the target analyte. The transduction material may be implemented in the sensing element as at least a single nanowire, nanorod, nanotube or nanoparticle. In some embodiments, the transduction material may be implemented in the sensing element as more than two nanowires, nanorods, nanotubes nanoparticles or combinations thereof interconnected in a network. The network may be random or an aligned array.

The transduction material is not necessarily limited to one type of material and may be, for example carbon nanotubes (CNTs), silicon nanowires, semiconducting polymers (e.g. polyanilines, polythiophenes) and mixtures thereof.

In a preferred embodiment, the transduction material comprises CNTs. CNTs may be metallic CNTs (m-CNTs), semiconducting CNTs (sc-CNTs) or mixtures thereof. The CNTs may be single-walled (SWCNTs), multiwalled (MWCNTs) or few-walled (FWCNTs). CNTs enriched in sc-CNTs are preferred. SWCNTs are preferred, especially SWCNTs enriched in sc-SWCNTs. The CNTs may come from any convenient source of CNT preparation. The SWCNTs may comprise raw (about 0.6 to 2.2 nm average diameter) SWCNTs prepared from HiPco, CoMoCAT, CVD, arc-discharge, laser-ablation or plasma processes. Enrichment of the SWCNTs in sc-SWCNTs may be accomplished by generally known methods, for example dispersing methods such as those methods involving polymer wrapping, for example with conjugated polymers such as polyfluorenes. Further, chirality separated sc-SWCNTs (single chirality semiconducting single-walled carbon nanotubes) may be used to differentiate sensing elements, i.e., a sensing element built on a given dielectric substrate will have a different response if the semiconducting channel is composed of (n1,m1) SWCNTs (where n and m index are commonly used in the literature to identify a SWCNT with given diameter and helicity) as compared to a sensing element where the semiconducting channel is composed of (n2,m2) SWCNTs as these nanotubes have different electronic band structures and energy bandgaps.

The target analyte is preferably a gas, liquid, vapor or mixture thereof. The target analyte is preferably any compound sufficiently volatile to form a vapor or gas at a temperature and pressure at which the sensing device is to be used. Some examples of target analytes are moisture, volatile organic compounds (VOCs, e.g. aromatics), amines, $C_{1-8}$ alkanes, air pollutants (e.g. CO, $CO_2$, $NO_x$, $O_3$, $H_2S$, $SO_2$, formaldehyde), pesticides (phosphine, bromomethane), chemical warfare agents (Sarin, mustard gas, phosgene), solvents ($CHCl_3$, benzene), industrial hazards ($NH_3$, $AsH_3$, $Cl_2$, HCN, $SiCl_4$), disease markers (NO, acetone), alcohols and drugs (including degradation byproducts) or mixtures thereof. In some embodiments, the target analyte may be present in a vapour comprising a mixture of constituents of ambient air or breath, namely $N_2$, $O_2$, $CO_2$, $H_2O$ and, in trace amounts, $NO_x$, $O_3$, $SO_2$, CO, etc., where any of the constituents may act as an interference to target analyte detection.

To fabricate a sensing element, a film of transduction material is brought into contact with an electrode pair on a substrate (resistor), a single electrode capacitively coupled to second electrode (capacitor), or an electrode pair on a substrate capacitively coupled to a gate electrode (transistor). A film of the transduction material is fabricated using a transduction material source in liquid form deposited by spin coating, drop casting, aerosol spraying, electrospraying, gravure printing, inkjet printing, or a transduction material source in dry form deposited by contact transfer, electrospraying. The electrodes are deposited prior to or after the transduction material film using microfabrication process such as metal evaporation and lithography or a printable process such as inkjet printing or gravure. A dielectric layer for the substrate or gate electrode is obtained using similar process if the dielectric material is a polymer or an inorganic/polymer combination. Inorganic dielectrics are more generally obtained from physico-chemical deposition methods.

Individual sensing elements are assembled into an array to form a sensing device. A sensing array is a collection of sensing elements yielding at least the same number of transduction signals to an analyte (e.g. gas, liquid or vapor) as the number of elements regardless of the number, shape and positioning of the elements. The simplest array is a 1×2 array comprising two sensing elements, one sensing element having a dielectric substrate comprising a different dielectric material than the dielectric substrate of the other sensing element. However, the at least two sensing elements may be in an array of any number of sensing elements greater than 2. Larger arrays of sensing elements are possible where the dielectric materials and semiconducting materials of the individual sensing elements are chosen to provide the widest variations in sensing element responses. The number of sensing elements in the array may be arbitrarily large, with 2, 4, 8, 16, 32, 64, 128, 256, 512, 1024, etc. being the most common configurations. Redundancy may also be provided, meaning that the same sensing element may be present any multiple of times in the array.

In one embodiment, the sensing device is designed to be selective for a single target analyte. To this end, the device comprises an array of sensing elements where one type of sensing element has an interaction strength with the target analyte that is different than the other type of sensing element. For example, in a humidity sensor comprising two sensing elements, a first sensing element has a hydrophilic substrate and a second sensing element has a hydrophobic substrate. In another embodiment, the sensing device is designed to be selective for a set of target analytes. To this end, the device comprises an array of sensing elements where there are types of sensing elements in the array having different interaction strengths with each of the target analytes, the interaction strengths being different than the interaction strengths of other types of sensing elements in the array with each of the target analytes.

In another embodiment, the different dielectric materials comprise a plurality of dielectric materials, one of the dielectric materials having an effect on transduction in the device of a nature different than the nature of the effect on transduction of the other dielectric materials. For example, one of the dielectric materials may have a different effect on how the target analyte shifts the Fermi level of the carbon nanotubes in comparison to the other dielectric materials, while one of the other dielectric materials has a different interaction strength with the target analyte than the other dielectric materials.

Arrays of sensing elements may be assembled in a suitable configuration. In a transistor configuration, transfer characteristics (e.g. drain-source current as a function of the gate-source voltage) and output characteristics (e.g. drain-source current as a function of the drain-source voltage) can be collected for any arbitrary voltage range. As target analyte concentration around the sensor changes, the change in concentration is primarily reflected in a change of current, voltage or resistance in the circuit. The change in analyte concentration may also be followed using parameters derived from current, voltage, charge, capacitance or resistance data. For example, when operated in a transistor configuration, the following parameters, but not exclusively, may be computed and followed as a function of concentration: the threshold voltage, the hysteresis, the subthreshold slope or swing, the hole and electron mobilities, the ON and OFF currents, the ON/OFF current ratio, etc.

The primary parameters and derived parameters from the sensing array may be collected in a set and analyzed using multivariate analysis, such as principal component analysis, partial least-squares, canonical-correlation analysis and factor analysis, to relate the analyte concentration to the array's set of responses. Machine learning, clustering, neural networks, regression and pattern recognition are other data analysis techniques that can be implemented.

Other methods of imparting variations to the sensing elements may be used in conjunction with using the dielectric substrates comprising complementary dielectric materials. Such other methods may include, for example, coating the transduction material with chemically selective thin films, chemically functionalizing the transduction material covalently or non-covalently, decorating sidewalls of the transduction material with nanoparticles, combining the transduction material with another transduction material and chemically functionalizing the substrate or contact electrodes. Alternatively or additionally, electrode materials in the sensing device may be changed to further tune the electronic properties of the transduction material.

EXAMPLES

Example 1

Referring to FIG. 1, a sensing device 1 comprises a transducer array 10 having a 2×2 array of transistors on chips 2, 4, 6, 8 acting as sensing elements. The chips 2, 4, 6, 8 comprise dielectric substrates on which are deposited electrode pairs 9 (only one labeled) electrically linked by electrical leads 5 (only one labeled) to electrical contacts 7 (only one labeled), the electrical contacts 7 electrically linked to pins 12 (only one labeled) of the device 1. Along with a third electrode (a gate electrode 11 (only one labeled)) beneath the dielectric substrate, each electrode pair 9 (source and drain electrodes) forms a transistor. Each of the chips 2, 4, 6, 8 comprises a layer of sc-SWCNT deposited on the substrate. Each chip 2, 4, 6, 8 has a substrate comprising a type of dielectric material different from the dielectric materials of the substrates of the other chip 2, 4, 6, 8. The different dielectric materials have different interaction strengths with one analyte or a set of target analytes.

When operated in a transistor configuration such as illustrated in FIG. 1, one or more parameters may be computed and followed as a function of concentration to provide a measure of the different interaction strengths with the analyte. Such parameters include, but are not limited to, threshold voltage, hysteresis, subthreshold slope or swing, hole and electron mobilities, ON and OFF currents and ON/OFF current ratio.

Figure 2:
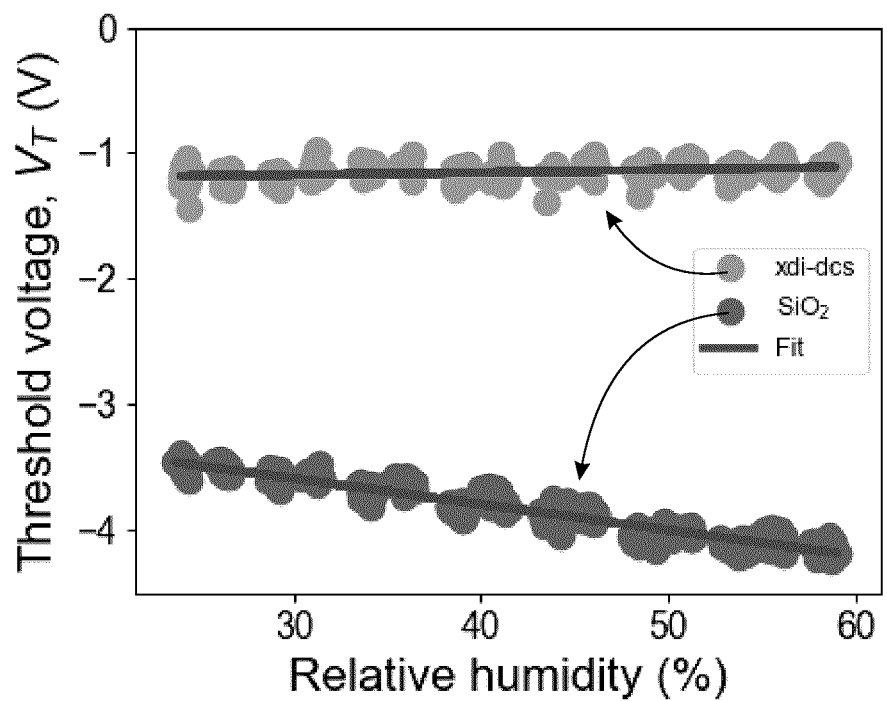
FIG. 2 depicts a graph showing the dependence of transistor threshold voltage, $V_T$, (V) on relative humidity (%) for paired sensing elements having substrates comprising $SiO_2$ (hydrophilic) and PVP-pMSSQ (hydrophobic).

Applying the design of the sensing device to humidity detection, hydrophilic silicon dioxide ($SiO_2$) was used as dielectric substrate for one transistor and hydrophobic poly(vinyl phenol)-poly(methyl silsesquioxane) (PVP-pMSSQ; Xerox xdi-dcs) was used as the polymeric dielectric substrate for the other transistor. FIG. 2 shows the dependence of transistor threshold voltage, $V_T$, (V) on relative humidity (%) for a 2×1 array of transistors having substrates comprising $SiO_2$ (lower plot) and PVP-pMSSQ (upper plot). The threshold voltage for the $SiO_2$-based transistors lowered as relative humidity increased while the threshold voltage for the PVP-pMSSQ-based transistors remained essentially the same. Properly chosen materials used as a dielectric substrate respond differently to different analytes.

Figure 3:
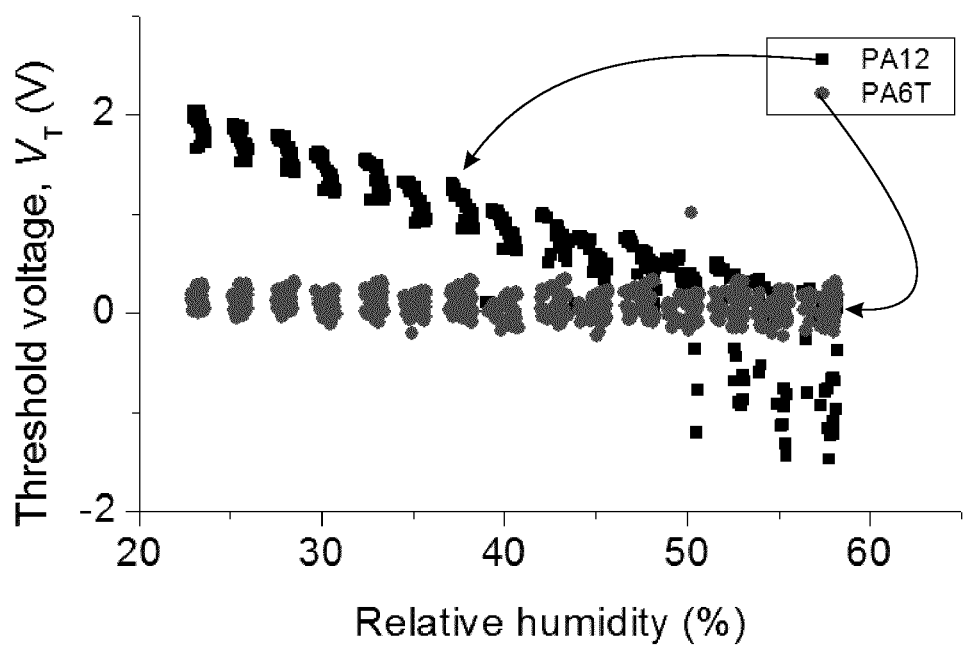
FIG. 3 depicts a graph showing the dependence of transistor threshold voltage, $V_T$, (V) on relative humidity for paired sensing elements having substrates comprising polyamide, PA12, (hygroscopic) and polyphthalamide, PA6T (less hygroscopic).

In another example, the design of the sensing device was applied to humidity detection by targeting hygroscopicity rather than simply hydrophilicity. The dielectric substrates used were polyamide PA12, which is hygroscopic, and polyphthalamide PA6T, which is less hygroscopic. FIG. 3 shows the dependence of transistor threshold voltage, $V_T$, (V) on relative humidity (%) for a 2×1 array of transistors having substrates comprising PA12 (upper plot) and PA6T (lower plot). The threshold voltage for the PA12-based transistors lowered as relative humidity increased while the threshold voltage for the PA6T-based transistors remained essentially the same.

Figure 4:
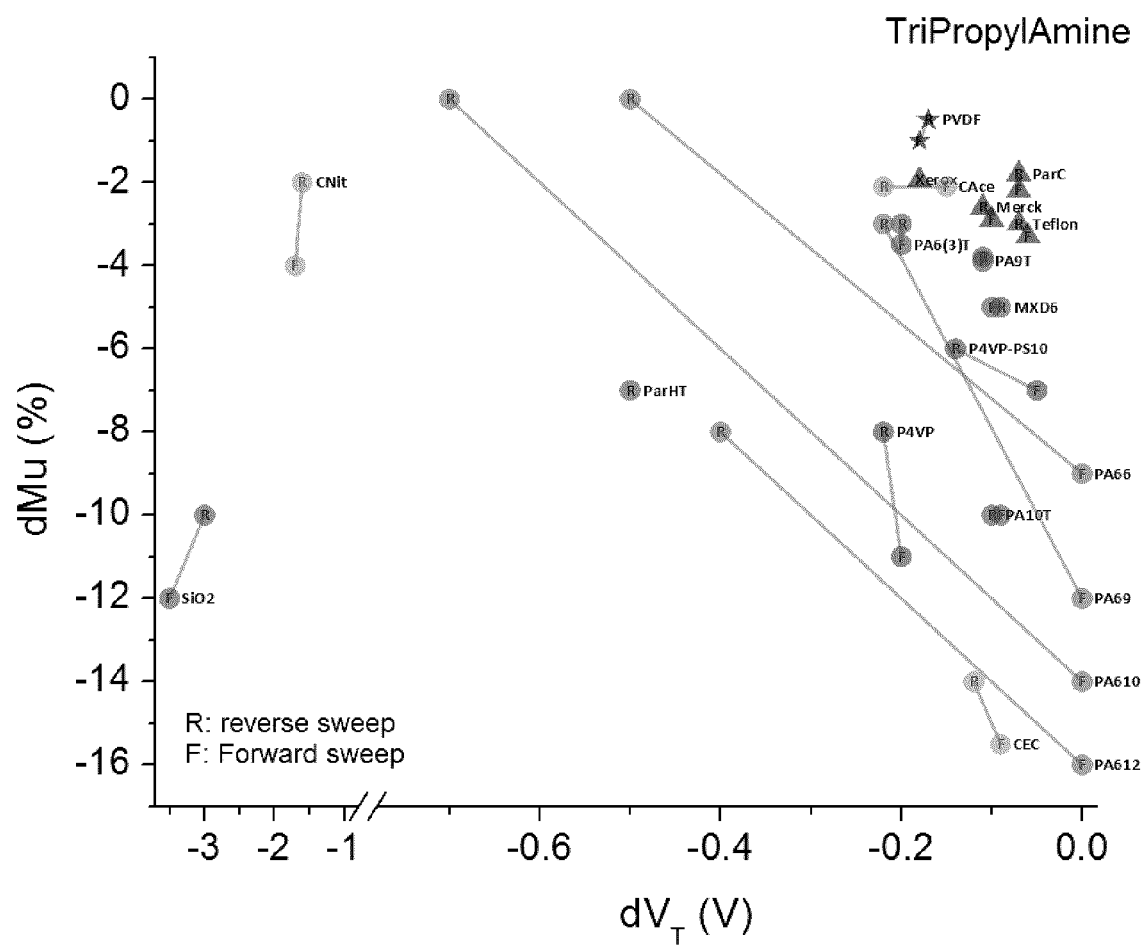
FIG. 4 depicts a plot showing response to tripropylamine vapor of a series of transistors comprising different dielectric substrates, with changes in mobility (dMu (%)) on the left axis and changes in threshold voltage ($dV_T$ (V)) on the bottom axis.

In another example, the design of the sensing device was applied to detection of tripropylamine vapors. The sensing device comprised an array of transistors comprising 20 different dielectric substrates. The dielectric substrates were: silicon dioxide ($SiO_2$); cellulose nitrate (CN); poly(vinyl phenol)-poly(methyl silsesquioxane) (Xerox xdi-dcs); cellulose acetate (CA); Parylene C (ParC); Merck D139; polytetrafluoroethylene (Teflon™); polyvinylidene difluoride (PVDF); polyphthalamide 6(3)T (PA6(3)T); polyphthalamide 9T (PA9T); polyamide 66 (PA66); polyphthalamide 10T (PA10T); polyamide 69 (PA69); polyamide 610 (PA610); polyamide 612 (PA612); polyphthalamide MXD6 (MXD6); poly(4-vinyl pyridine) (P4VP); poly(4-vinyl pyridine)-polystyrene 10 (P4VP-PS10); cyanoethyl cellulose (CEC); and, Parylene HT (ParHT). As seen in FIG. 4, changes in mobility (dMu (%)) and changes in threshold voltage ($dV_T$ (V)) were recorded for each transistor, each transistor behaving in a different manner. This pattern of behavior for the array can be correlated to the concentration of tripropylamine for any one or more of the transistors, and the array used to detect tripropylamine in unknown vapor samples. The results also show that any two or more of the dielectric substrates tested may be used in a sensing device to successfully detect tripropylamine.

The use of multiple dielectric materials in a device array architecture for the purpose of sensing specific analytes has been shown in Example 1. Each dielectric substrate responds differently to different analytes allowing for discrimination and selective detection of the analyte. While application to humidity and tripropylamine sensing have been exemplified, the principles can be extended to selective detection of other analytes.

Materials and Methods for Examples 2-5:

Bottom Gate Transistor Fabrication: Substrates were cleaved from degenerately doped Si wafers coated with a 30 nm oxide (or 1000 nm for $SiO_2$ based transistors) to eliminate gate leakage from pinholes in the polymer films (in general, an oxide layer was not required but still was considered a practical solution to rapidly screen through many polymers). The Si substrate served as the gate electrode. Most polymers came in solid form and most were dissolved in DMF, except for nylons which were dissolved in m-cresol, and fluorinated polymers which were purchased as solutions. Polymer solutions were spin coated with the weight concentration (5-10%) and spin speed (1000-2000 rpm) adjusted to obtain smooth layers in the 200-800 nm thickness range. An air gun (100° C. set point) positioned above the sample during spin coating significantly improved film morphology for DMF and m-cresol formulations. After coating, samples were left on the hot plate at 110° C. for 20 min. Aliphatic nylons were annealed above their glass transition temperatures and quickly cooled to reduce crystallinity (as seen by haze). Parylene-C and -HT coatings were obtained from SCS (Specialty Coating Services, a Kisco company). Source and drain electrodes were made by electron-beam evaporation of Ti (5 nm) and Au (100 nm) through a metallic stencil mask in close contact with the sample. The channel dimensions were 1000 μm×40 μm. Carbon nanotubes were deposited on top of the electrodes (see below).

Carbon nanotubes dispersions: The dispersions were prepared from raw SWCNTs material supplied by Raymor Nanotechnologies (RN-000, plasma process, diameter around 1.3 nm). The process, previously reported by our group, consists of a selective extraction of sc-SWCNTs with conjugated polymer (poly(9,9-didodecylfluorene), PFDD) in toluene solvent. The mixture (PFDD to SWCNT weight ratio of 1.0/1.0 and a nanotube concentration of 0.8 mg/mL) was horn sonicated for 30 min (Branson sonifier 250) followed by 30 min centrifugation (about 18,000 g). This step was repeated 5 times using the sediment from the previous centrifugation. Silica gel (at 1 mg/mL) was added to the combined five supernatant solutions and the mixture was bath sonicated (Branson 2510) for 40 min, followed by standing for 3 h, and then 30 min centrifugation (about 18,000 g). The supernatant was filtered using a Teflon membrane with 0.2 μm pore size (Sartorius Stedim Biotech) and rinsed with toluene to remove excess polymer. The collected sc-SWCNTs were dispersed in toluene using bath sonication for 5-10 min at a concentration of 0.48 mg/mL and a polymer to nanotube weight ratio of 2.4.

Carbon nanotube deposition: SWCNTs wrapped with conjugated polymers have good adhesion properties to $SiO_2$ dielectric surface ($SiO_2$/Si substrates) and transistors made from soaking show high mobility combined with high ON/OFF ratio. This is however not the case for every dielectric surface. As reported for aerosol deposition, carbon nanotubes present weak adhesion to materials with a low surface energy, for example fluorinated polymers. Aerosol being a dry process could effectively overcome that problem. Stable nanotube networks can also be formed on any materials by soaking, provided a voltage is applied (so-called E-soak) between an electrode and the substrate. A detailed study of the process is still required but the magnitude of the voltage and its polarity affected SWCNT network (coverage and morphology). For a small circular electrode (0.5 mm radius), 35 V on a 1 mm gap appeared suitable. Higher voltages were found to lead to vortices in the solution which sometimes caused delamination of deposited SWCNT films. For a 1 μg/mL SWCNT concentration, deposition times are on the order of minutes (2-5 min) and the carbon nanotubes deposit mainly under the electrode. For $SiO_2$/Si and other surfaces where soaking alone is sufficient, E-soaking at <1 μg/mL provides 10 to 100-fold more coverage under the electrode.

Electrical measurements. All the measurements were performed in air ambient, either on individual transistors in a probe station or on several transistors mounted in a chip carrier. A dual channel source-measure unit (Keithley™ 2602B) was used to supply both gate and drain-source biases and to measure transistor and leakage currents at a sweep rate of 1.2 V/s. For multi transistor measurements, a 20-channel multiplexer (Keithley™ 3706A) was used to switch between transistor drain contacts while source and gate contacts were made common to all.

In a transistor configuration, transfer characteristics (e.g. drain-source current as a function of the gate-source voltage) and output characteristics (e.g. drain-source current as a function of the drain-source voltage) can be collected for a given voltage range. As a target analyte is introduced, the measured current, voltage or resistance in the sensor circuit also changes. The change in analyte concentration may also be followed using parameters derived from current, voltage, charge, capacitance or resistance data. For example, when operated in a transistor configuration, the following parameters may be computed and followed as a function of concentration: the threshold voltage, the hysteresis, the subthreshold slope or swing, the hole and electron mobilities, the ON and OFF currents, the ON/OFF current ratio, etc. The large majority of polymer films were not tested for their dielectric response (capacitance and dielectric loss); transconductance ($dI/dV_g$), rather than mobility, is thus reported.

Environmental measurements: Two types of environmental testing were performed, humidity response and volatile compound response. In the former, several transistors were mounted and wire bonded to a chip carrier placed inside a small enclosure (approximately 10 mL volume) with gas inlet and outlet ports. Humid air between 10 and 70% RH was generated with a commercial humidity generator (GenRH-Ambient, Surface Measurement Systems) using compressed air at a flow rate of 100 sccm. Humidity was stepped in 5% increments and stabilized before electrical measurements. During electrical measurements, each transistor is sequentially biased and the gate voltage swept to obtain a complete transfer curve. Between humidity steps, the transistors were kept at ground. RH and temperature were monitored at the sample chamber using a commercial sensor (Sensirion™ SH11).

In the vapor sensing experiments, four manually controlled bubblers were mounted in parallel along with a bypass line (SI). Room air was supplied at 500 sccm to the manifold using a small diaphragm pump. In a measurement series, the bypass valve remained continuously open while each liquid-containing bubbler was sequentially opened to supply a vapor to the enclosed sample probe station. The parallel gas flow in the bypass and bubbler lines ensured minimal flow disruption during manual opening/closing of the valves. The bubbler consisted of a 5 mL vial with its plastic cap mounted with concentric brass tubing for vapor inlet and outlet. The inlet tube set above the liquid (rather than bubbling into the liquid) was found sufficient to provide enough analyte for detection. Under similar measurement conditions, it was estimated that a 6 sccm air flow with methanol gave ppm levels exposure. We can estimate that high ppm level exposures were achieved with liquid having highest vapor pressures (acetone). For amine liquids, dilute mixtures with toluene were prepared to bring the transistor response to magnitudes similar to other vapors. Solutions with a partial pressure of 0.02 mmHg for TPA, TEA, IBA and dIBA appeared adequate for this experiment. Such low levels may correspond to doses at the low ppb levels.

Example 2

Figure 5:
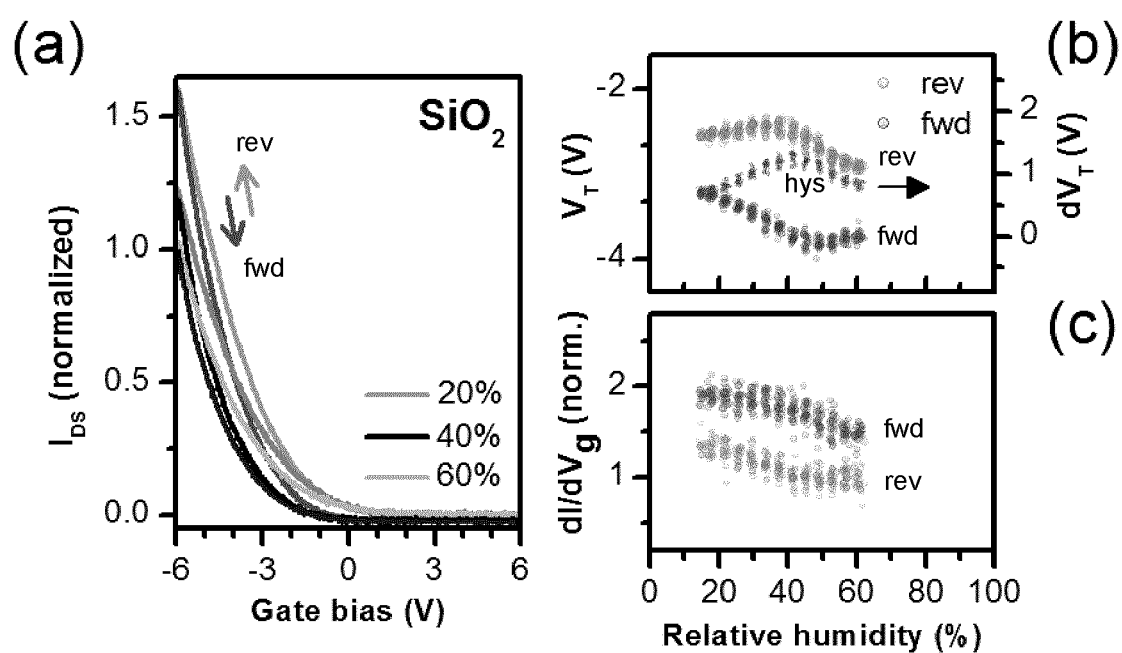
FIG. 5 depicts graphs showing performance of carbon nanotube network transistors on $SiO_2$ gate dielectric substrate, where (a) shows transfer characteristics taken at three levels of relative humidity (RH) normalized to 60% RH.

Experiments were performed to identify electronically suitable polymeric dielectric materials where the physical and chemical processes at the interface and within the dielectric substrate are minimized, and which produce little gate hysteresis while having excellent temporal stability in carbon nanotube network field-effect transistors (CNN-FET) bottom gate configuration In a first set of experiments, humidity cycles on a CNN-FET built were performed on different gate dielectrics. As the prototypical carbon nanotube transistor, FIG. 5 shows how the electrical characteristics of a sc-SWCNT percolation network deposited on 1000 nm thick $SiO_2$ dielectric layer is affected by varying relative humidity (RH) in normal air ambient. In these experiments, relative humidity (RH) is stepped and stabilized while the transistor remains electrically grounded, followed by measurement at a set RH value. The three transfer curves in FIG. 5(a) reveal a moderate change upon cycling between 20 and 60% RH. Of note, the hysteresis (hys) between reverse (r-sweep (rev), towards minimum $V_g$) and forward (f-sweep (fwd), towards maximum $V_g$) sweeps is counter clockwise and comparatively small due to the smaller range of applied gate bias and the thick dielectric layer (1000 nm $SiO_2$). Qualitatively, the curves display an increased transconductance ($dI/dV_g$, the slope of I vs $V_g$ in the accumulation regime, $|V_g-V_t|>0$) along with a positive shift of threshold voltage ($V_t$) as the humidity drops to 20%. FIG. 5(b) and FIG. 5(c) plot the two parameters obtained from linear fits as function of RH for ten successive cycles. The scatter of data is sufficiently small for trends to be clearly identified. The shift of $V_t$ is markedly different for r- and f-sweeps, with the f-sweep initially unaffected by a reduction of RH from 60 to 40% while the r-sweep presents a large shift. Below 40% RH, the opposite is observed where the r-sweep is minimally affected by a reduction of RH. Consequently, a pronounced maximum around 40-50% RH is observed in the $V_g$ hysteresis. Interestingly, the transconductance mirrors $V_t$ where the r-sweep is initially independent of RH followed by a linear increase below 40% RH. For both sweep directions the transconductance increases by about 50% over the 20-60% RH range. The present result follows the general trend observed in individual nanotube transistors.

Figure 6:
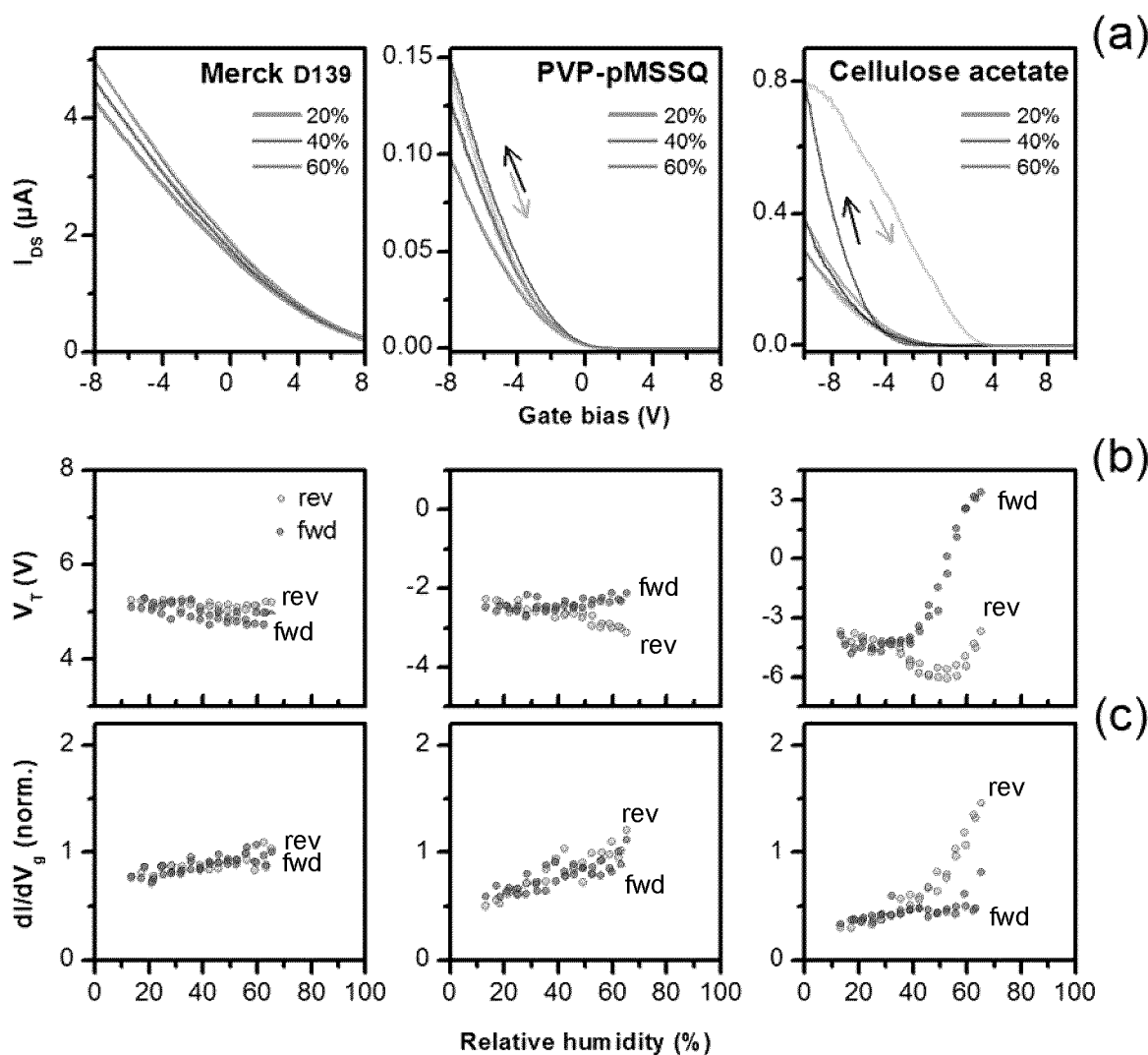
FIG. 6 depicts graphs showing performance of carbon nanotube network transistors on three polymer gate dielectric substrates, where (a) shows transfer characteristics taken at three levels of relative humidity (RH)

A total of 43 polymers were surveyed in like manner, and FIG. 6 highlights some of the salient features. The deposition method for sc-SWCNT networks ensured good surface coverage with similar current levels in all cases. In order to enable some degree of comparison, polymer film thicknesses were maintained around 400 nm, where possible, and Vg sweep ranges were adjusted to partially account for differences in thickness and dielectric constant. For some polymeric materials (cellulose nitrate, Parylene HT), carbon nanotube adhesion appeared markedly more efficient while for others (low surface energy polymers PVP-pMSSQ, Merck D139, Teflon™ AF), longer deposition times were required to achieve similar current values. For the latter, electrostatically assisted deposition (E-soaking) was necessary to achieve sufficient film adhesion without delamination upon drying.

Carbon nanotube network transistors can be classified in three main categories with regard to the measured hysteresis: advancing, lagging or free. Hysteresis-free transfer characteristics are obtained when the configuration of space charge or polar moieties is static or dynamically tracks the applied gate bias. In the survey of polymers, over a dozen polymer dielectrics were identified, which fall into the hysteresis-free category, including fluorinated polymers (Teflon™ AF, Merck D139, Parylene HT), aromatic nylons (polypthalamide), PVP-pMSSQ and Parylene C. Data for Merck D139 and PVP-pMSSQ is shown in FIG. 6(a) and indeed exhibits hysteresis-free traces at the RH levels tested. For transistors with carbon nanotubes directly exposed to air ambient, this is only possible if water, oxygen and possibly other gases can be excluded from the immediate nanotube surroundings. For hydrophilic $SiO_2$, the water/oxygen redox couple and dissolved ionic species induce the lagging hysteresis seen in FIG. 5. Polymer dielectrics that present a similar characteristic include P4VP, P4VP-PS10 and Nylon™ MXD6.

A dielectric can have a significant polarizability attributable to mobile functional groups and electron-rich chemical bonds. Although this yields an increased dielectric constant, and thus low operation voltages in those transistors, it often leads to a large advancing hysteresis, the most extreme case being ferroelectric materials. Aliphatic nylons (polyamide), PVDF and cellulose variants (cyano ethyl) are examples of materials with slow polarization. When those materials are used as gate dielectrics for CNN-FETs, the reverse sweep is advancing the forward sweep. Data showing an advancing hysteresis from cellulose acetate is here presented in FIG. 6(a). Other than for memory applications, those polymers are generally discounted for use in electronic components, especially for transistors. However, the present data shows that such polymers can be very useful for gas sensing and can be an integral part of a sensor array comprised of a complementary set of polymer dielectrics.

In a second set of experiments, the ability of the surveyed polymers to partially discriminate between analytes was determined. Following the analysis presented in FIG. 5, FIG. 6 presents the electrical response of transistors made on three different polymer dielectrics to varying levels of humidity in ambient air. The first two, Merck D139 and PVP-pMSSQ, are hydrophobic polymers with a large water contact angle, 109° and 89°, respectively. Both present monotonic change of threshold voltage over the 10-65% RH range, with a magnitude that is smallest for Merck D139 but not markedly different from $SiO_2$. For the transconductance however, the two polymers show a decrease rather than an increase for hydrophilic $SiO_2$ under dryer ambient air. The change is remarkably linear and also less pronounced for Merck D139 (−0.4% per % RH) compared to PVP-pMSSQ (−1% per % RH). The interaction of water molecules is believed to occur either directly at the nanotube's surface or, more likely, at grooves and interstitial adsorption sites. The small variation with respect to RH could therefore be attributed to dielectric screening by polar molecules in the immediate nanotube surroundings, the equivalent of an increased dielectric constant. The room temperature reversibility supports a scenario involving weak van der Waals interactions.

The most dramatic result is obtained for polymers with advancing hysteresis. In FIG. 6(b), data for cellulose acetate (52° contact angle) is presented. As the RH drops from 65%, the large hysteresis rapidly shrinks to reach 0 V near 35% RH and the transfer characteristics remain hysteresis-free down to 10% RH. At the same time, the transconductance drops significantly (sevenfold for the f-sweep). Compared to $SiO_2$, cellulose acetate may be easily dehydrated and hydrated, reversibly as successive RH cycles illustrate (data not shown). In the hydrated state, polar moieties and water molecules contribute more significantly to the advancing hysteresis. The experiments were performed in a quasi-static mode where sufficient time (15 min. between 10% RH increments) was allowed for the polymer to equilibrate with its environment.

Figure 7:
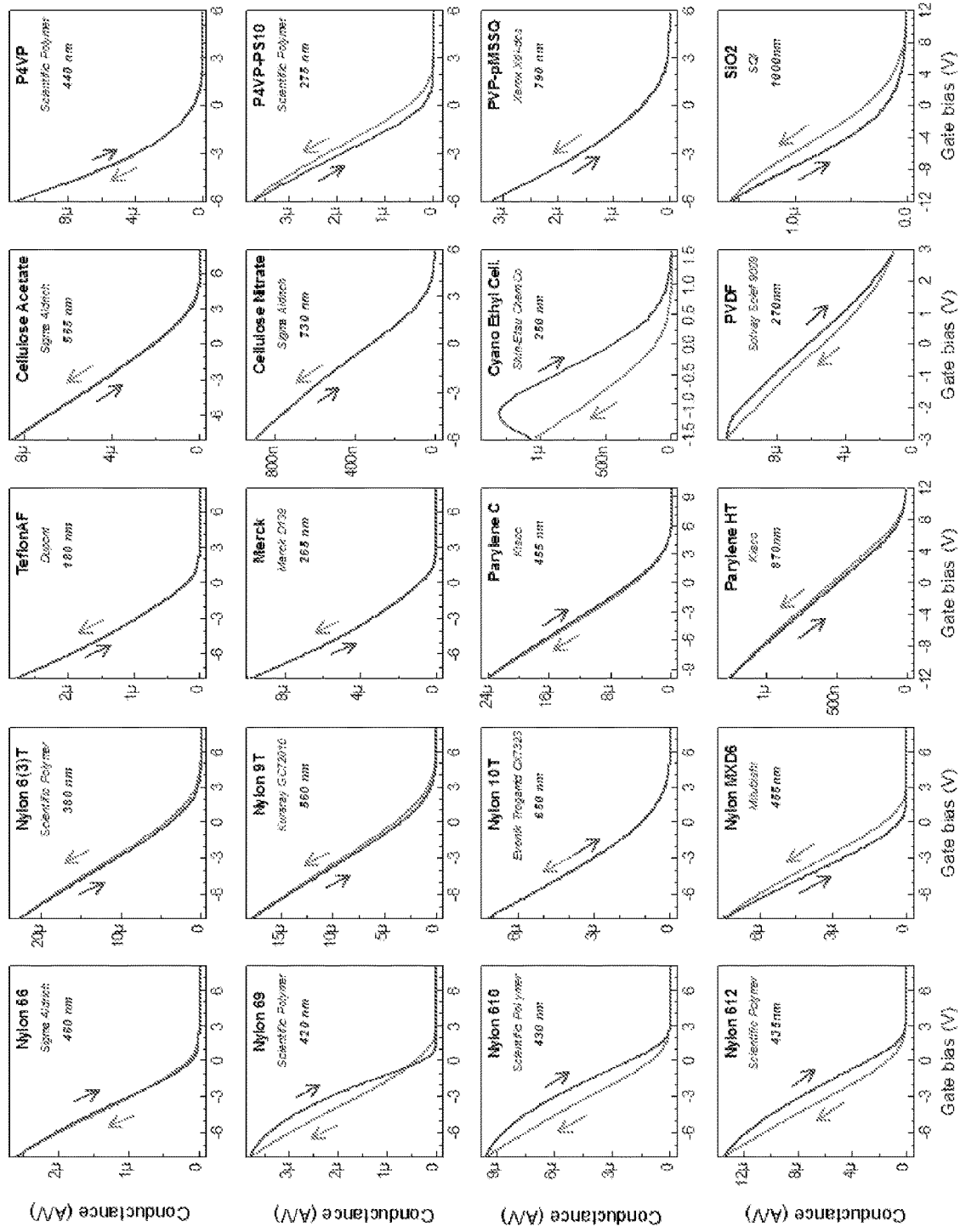
FIG. 7 depicts graphs showing transfer characteristics for carbon nanotube transistors on a series of polymer gate dielectric substrates compared to an $SiO_2$ gate dielectric substrate.
Figure 8:
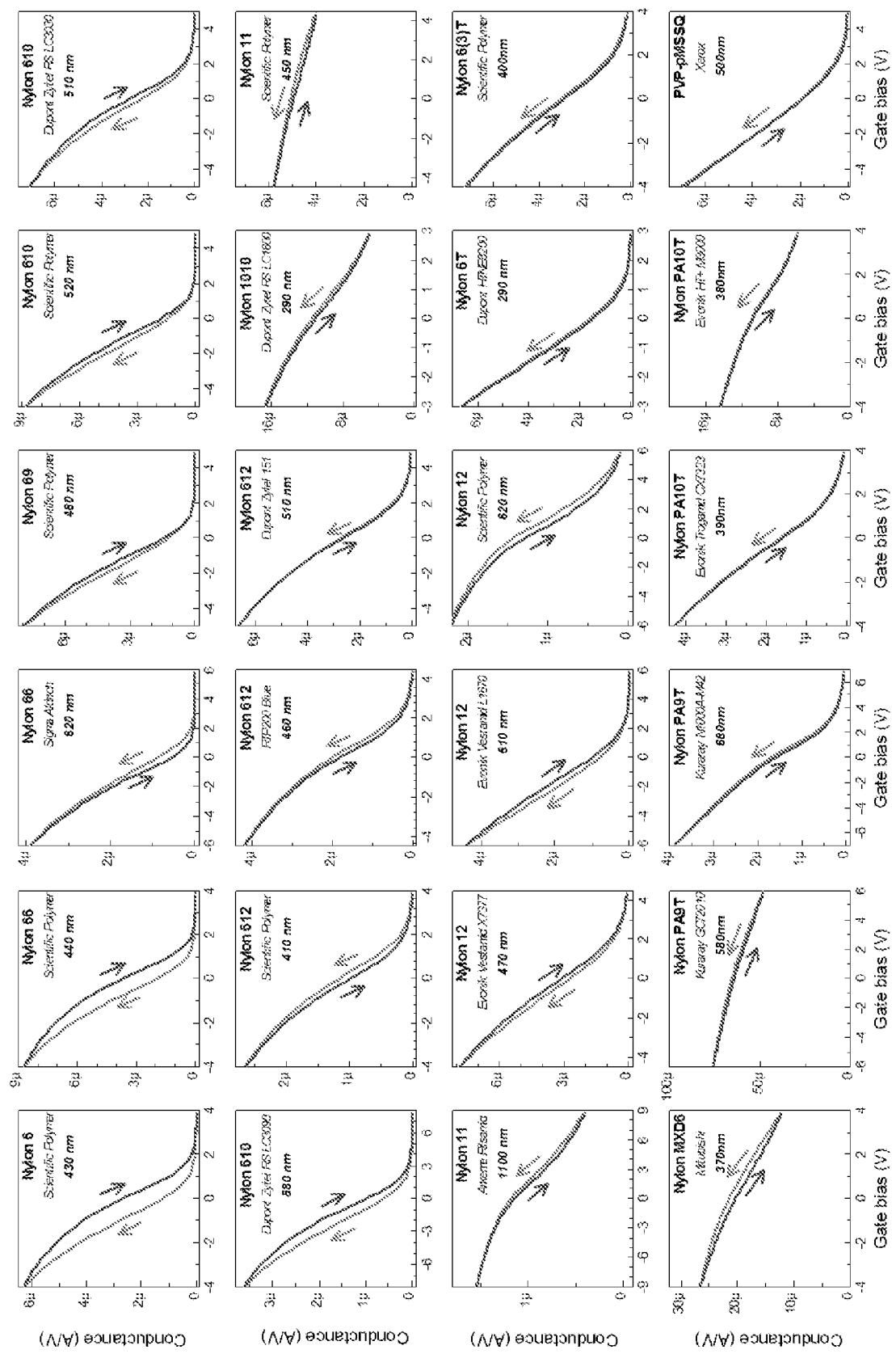
FIG. 8 depicts graphs showing transfer characteristics for carbon nanotube transistors on a series of nylon gate dielectric substrates compared to a PVP-pMSSQ gate dielectric substrate.

In the survey of polymers, special attention was paid to the threshold voltage, with a view to reaching the transistor's depletion operation mode at $V_g=0$ V without an encapsulation layer. The data in FIG. 7 and FIG. 8 show several examples of transistors with $V_t<0$. A subset of polymeric materials was identified (nylon, P4VP, cellulose acetate) and can be further considered in the context of printed electronics devices, other than gas sensors.

Example 3

Figure 9:
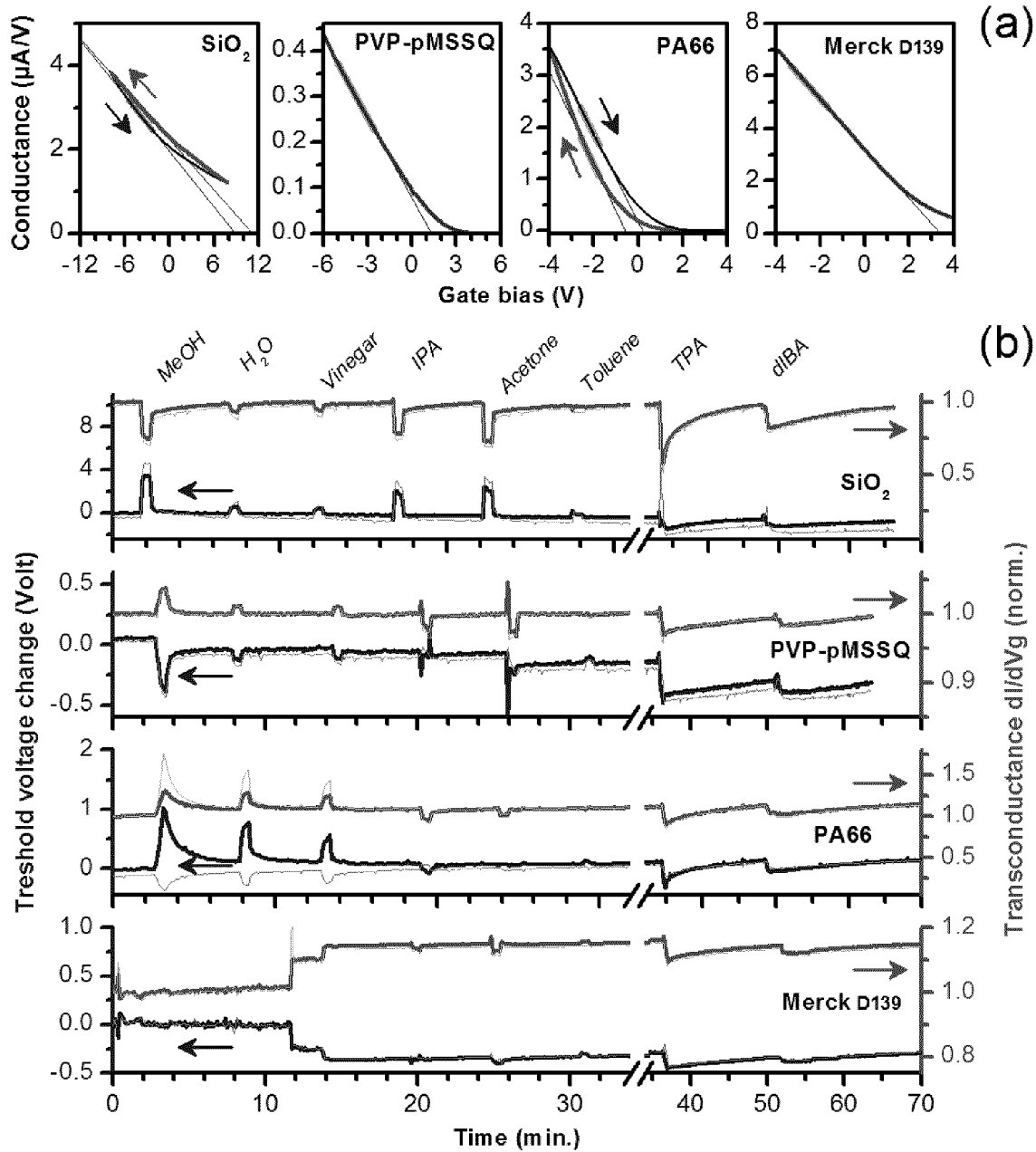
FIG. 9 depicts graphs showing performance of carbon nanotube network transistors exposed to volatile compounds.
Figure 10:
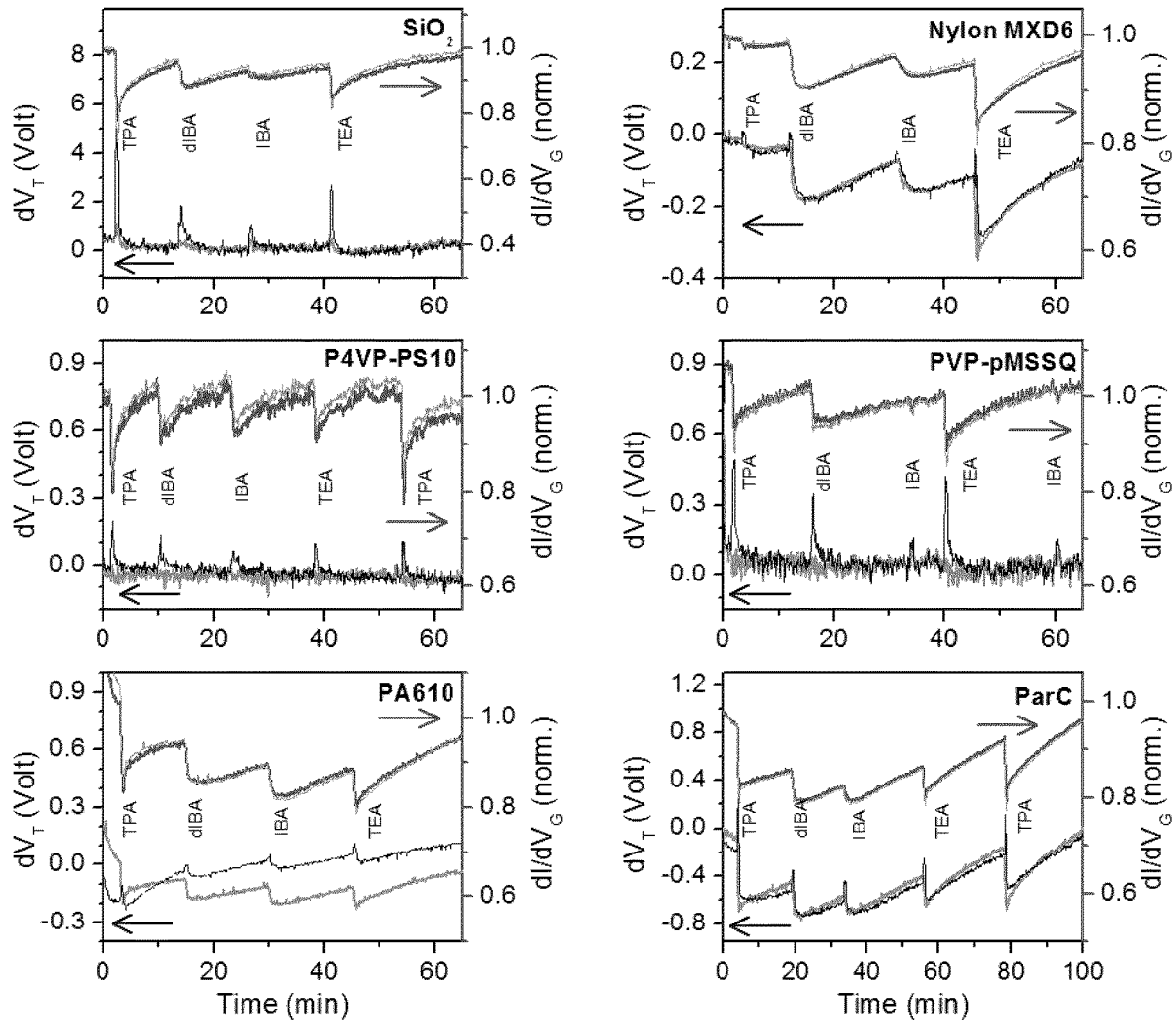
FIG. 10 depicts graphs showing evolution of transistor threshold voltage and transconductance for six transistors with different gate dielectrics upon exposure to four volatile liquid amines (tripropylamine (TPA), diisobutylamine (dIBA), isobutylamine (IBA) and triethylamine (TEA)).

The effect of humidity levels on carbon nanotube transistors in ambient air described above provides clear evidence that the choice of dielectric substrate materials affects the gas sensing response. To further the demonstration, a set of transistors built onto different polymer dielectrics was exposed to a variety of volatile compound vapors. In this second set of experiments, measurements were continuously acquired while an analyte was pulsed. Selected results are presented in FIG. 9 and FIG. 10, where transfer characteristics were continuously acquired while vapors were mixed in with ambient air. As shown in FIG. 9(a), a linear portion of the transfer curve was fitted to extract $V_t$ and $dI/dV_g$ in real time. The duration of a gate sweep was 7 s and the exposure to analyte was approximately 35 s.

The four examples in FIG. 9 comprise the three hysteretic behaviors described above. The time traces for $SiO_2$ in FIG. 9(b) reveal an upshift of $V_t$ for polar solvents and acetic acid (10%, vinegar), and a downshift of $V_t$ for the two amines (tripropylamine and disobutylamine), which points to an acid/base effect on $V_t$. The response was reversible in all cases and fast recovery was seen except for the two amines where $V_t$ returned to its original value after 5-10 min. Such a recovery compares favorably well with other CNT sensors operated at room temperature. It is possible that the continuous sweep method also contributes to resetting the transistor to its original ambient air values. For $dI/dV_g$, a reduction is observed for all 8 analytes in FIG. 9. For methanol, isopropanol and acetone, the recovery dynamics show two components, the fast component accounting for 70% of the recovery. The slow recovery, on the scale of a few minutes, is not seen on the trace of $V_t$. The complementarity of signals seen on $SiO_2$ based CNN-FETs uncovers a wealth of information available from transistor metrics. Compared to chemiresistors where resistance change and time dynamics are being tracked, at least four and up to eight transistor parameters and their respective dynamics provide good metrics for volatile compound sensing: $V_t$, $dI/dV_g$, $d\log(I)/dV_g$, $I_{On}/I_{Off}$, mainly from p-type conduction but potentially from n-type as well.

FIG. 9 also presents datasets obtained from transistors built onto three polymer dielectrics. PVP-pMSSQ, with the methylated silsesquioxane being at the exposed surface, is a hydrophobic polymer and, as expected from the humidity response in FIG. 6, displays a markedly different response than $SiO_2$ to polar solvents and acetic acid. For all volatile compounds, the shift in Vt is opposite in sign to $SiO_2$, except for toluene and amines where a similar upshift is observed. For methanol, the response and recovery are both slower than for $SiO_2$. Recovery to the two amine vapors is also slower for PVP-pMSSQ. The transconductance for PVP-pMSSQ presents some contrasting patterns. For $SiO_2$, $dI/dV_g$ a decrease is observed for all eight analytes, while for PVP-pMSSQ an increase is observed for methanol, water and acetic acid. Interestingly, the two alcohols, methanol and isopropanol have opposite $dI/dV_g$ changes.

The second polymer in FIG. 9 is a polyamide (aliphatic PA66) with an advancing hysteresis. Beyond some of the points already highlighted for PVP-pMSSQ and $SiO_2$, the r- and f-sweep for PA66 show an opposite shift of $V_t$ for methanol, water and acetic acid while $dI/dV_g$ is in phase (either decreases or increases) for the eight analytes. The polyamides (aliphatic nylon) were especially sensitive to methanol but not so much to acetone. This high sensitivity can be attributed to the ability of methanol to form hydrogen bonds with the nylon structure, specifically with —NHC (=O)— groups. Aromatic nylons (PA6T, PA10T, PA6(3)T and MXD6) on the other hand, did not show such high sensitivity to methanol, perhaps due to the denser packing of the polymer.

The third polymer in FIG. 9 is Merck D139, a hydrophobic fluorinated polymer with an even larger water contact angle than PVP-pMSSQ. Apparently, the different chemical nature (Merck, proprietary) of the fluorinated polymer still confers a strikingly different CNN-FET response to the eight analytes. It is essentially not responsive to methanol and water, but shows a pronounced, irreversible downshift of $V_t$ together with an increase of $dI/dV_g$ upon exposure to acetic acid, hinting at a strong affinity with the dielectric.

Example 4

Amines, especially ammonia, have been prototypical analytes for their pronounced effect on CNN-FET response. A set of five amines were investigated: triethylamine (TEA), tripropylamine (TPA), isobutylamine (IBA), diisobutylamine (dIBA) and 2-acetyl-3,5(6)-dimethylpyrazine (AdMPyr). With all tested gate dielectrics, a negative shift of $V_t$ was observed consistent with electron transfer from the amine along with a reduction of transconductance. For a given partial vapor pressure (0.02 mmHg, adjusted by diluting the amine with toluene), the response to the two tertiary amines was similar (TEA and TPA) in magnitude but was twofold larger compared to the secondary amine dIBA. The primary amine IBA generally presented a marginally smaller response. These amine-related results can be observed in FIG. 9(b) with complementary datasets presented in FIG. 10. Due to a very low vapor pressure, AdMPyr only caused a small change in the transistor response. The most notable difference in amine sensing came from the response time. Generally, the recovery was faster for tertiary amines and the timescale was dependent on the polymer dielectric. In FIG. 9(3b), $SiO_2$ shows the fastest response to TPA while Merck D139 is the slowest of all four dielectrics. Similar to graphene chemiresistors, the different time responses may be used to discriminate between analyte classes and subclasses. An even more powerful approach to chemical discrimination may come from the data analysis of multiple real-time transistor array signatures.

Example 5

The number of polymer dielectrics surveyed together with the number of analytes tested amounts to more than 400 transistor curves and at least twice as many time traces. Efforts in automating sensing combined with analysis methods for large datasets such as machine learning would speed up the materials screening process. Nevertheless, FIG. 11 captures the salient behaviors observed between polymer dielectrics. The qualitative results have been normalized with respect to tripropylamine (marked "R") with lighter/darker squares reflecting a weaker/stronger response in terms of change in $V_t$ and $dI/dV_g$ (only the magnitude is considered, not the sign change). Amines represent a good reference since they affect CNN-FETs through direct charge transfer (except for details described in the preceding paragraph), which is largely independent of the underlying dielectric. It is important to note that ambient air was simply flushed over solutions with sometimes more than tenfold difference in vapor pressure. In more rigorous experiments, dosing with known analyte concentrations will enable complete assessment of sensitivity and cross-selectivity.

As seen from FIG. 11, almost every surveyed volatile compound yields a different signature (columns) when considering all tested gate dielectric materials. Such behavior forms the basis of cross-reactive chemical sensor arrays, where pattern matching over a variety of nonspecific sensor elements enables chemical recognition, in analogy to the olfactory system. Alkanes and toluene here produce a weaker signal over a broad set of dielectrics, while polar molecules such as acetone, tetrahydrofuran and isopropanol have a signature generally comparable to TPA, to the exception of the enhanced response of PVDF to the former. The signature of methanol, as mentioned earlier, presents a hot spot with the aliphatic nylons. Even more degrees of freedom related to transistor parameters (transconductance, threshold voltage, subthreshold slope, and their time dependence over analyte exposure, etc.) could be used for pattern recognition instead of compounding the factors into a general response.

Sensor response and specificity to analytes emerge from variations in the device's transduction process. In a transistor, four causes of transduction signal modulation are possible: a shift of the Fermi level in the channel material, a modification of the Schottky barriers at the electrodes, a variation of the dielectric permittivity in the proximity of the channel material and a change in carrier scattering in the channel material. In the absence of analytes, substitution of the substrate dielectric can affect not only the gate capacitance but more importantly the Fermi level of the channel materials through the physicochemical nature of the different polymers. Under a given ambient, variations in interfacial charge trapping and binding affinity of atmospheric interferences (namely, water) and analyte modifies the chemical potential of the channel material through redox processes and/or electrostatics. Variations in the specific interaction strength of an analyte also perturb the dielectric environment, where the dielectric permittivity is modified either by the molecule displacement and change of orientation, or by plasticizing the dielectric interface. For SWCNTs, those indirect processes involving analyte and polymer dielectric have significant impact on the electronic transduction. This attribute may not be unique to SWCNTs but the effect is pronounced since electrostatics screening in 1D is known to be greatly reduced. Direct interaction of analytes with carbon nanotubes should, in the majority of cases, be convoluted with indirect contributions from the polymer substrate. Leaving the carbon nanotubes essentially bare on the substrate should insure optimum response times. There may be substrate materials (low and ultra-low k) which would mimic conditions found in freestanding films and would therefore maximize the relative contribution from the SWCNTs, a desirable situation when functional groups are added to the nanotube sidewalls.

The Examples illustrate how the role of the interfacial dielectric substrate material can be utilized in electronic sensing devices, especially carbon nanotube network field-effect transistors (CNN-FET) in the bottom gate configuration. Utilization of the dielectric substrate as the dominant vector of analyte interaction extends beyond the hydrophilic/hydrophobic dichotomy regarding humidity response. The Examples identify electronically suitable polymeric dielectric materials where the physical and chemical processes at the interface and within the dielectric substrate are minimized, and which produce little gate hysteresis while having excellent temporal stability, especially in carbon nanotube network field-effect transistors (CNN-FET) bottom gate configuration.

Further, the polymer dielectrics may be separated into three classes with respect to their humidity hysteresis behavior. For gas sensors, polymer gate dielectrics may be used to differentiate sensor elements and may therefore be utilized in a cross-reactive chemical sensor array for molecular recognition, where polymer gate dielectrics yielding a large hysteresis are an additional asset for analyte differentiation as an integral part of a sensor array. The Examples have systematically compared the response of CNN-FETs built atop various polymer dielectrics, using $SiO_2$ as the standard reference, in, first, varying humidity conditions, and, second, to a large set of volatile organic compounds (VC). The emerging signatures in the polymer-differentiated sensing element responses show applicability to a printed electronic nose.

The novel features will become apparent to those of skill in the art upon examination of the description. It should be understood, however, that the scope of the claims should not be limited by the embodiments, but should be given the broadest interpretation consistent with the wording of the claims and the specification as a whole.

The invention claimed is:

1. An electronic device for sensing a target analyte in a gas, liquid or vapor sample, the device comprising at least two sensing elements, each sensing element comprising an exposed layer of a transduction material supported on a dielectric substrate, wherein the dielectric substrate of at least one of the sensing elements comprises a different dielectric material than the dielectric substrate of at least one other of the sensing elements, the different dielectric materials providing a different sensing response according to one or more transduction modes.

2. The device of claim 1, wherein the one or more transduction modes comprises one or more of: a shift of the Fermi level of the sensing element; a modulation of the Schottky barrier of the sensing element; a change in the dielectric environment around the sensing element; and, a change in the charge carrier diffusivity of the sensing element.

3. The device of claim 1, wherein at least one of the dielectric materials has an effect on transduction in the sensing element of a nature different than the nature of the effect on transduction in another of the sensing elements comprising another of the dielectric materials.

4. The device of claim 1, wherein at least one of the different dielectric materials comprises silicon dioxide.

5. The device of claim 1, wherein at least one of the different dielectric materials comprises an organic polymer.

6. The device of claim 5, wherein the organic polymer comprises a polyamide, a polyvinylphenol, a polysilsesquioxane, a polyacrylate, a polyfluorinated alkane, a polystyrene, a polyvinylpyridine, a cellulose derivative, a poly(p-xylylene), a copolymer thereof or a blend thereof.

7. The device of claim 1, wherein the target analyte is humidity and one of the dielectric materials is hydrophilic and another of the dielectric materials is hydrophobic or one of the dielectric materials is hygroscopic and another of the dielectric materials is non-hygroscopic.

8. The device of claim 1, wherein the transduction material comprises carbon nanotubes, silicon nanowires, semiconducting polymers or mixtures thereof.

9. The device of claim 1, wherein the transduction material comprises single chirality semiconducting single-walled carbon nanotubes.

10. The device of claim 1, wherein the transduction material is implemented as at least a single nanowire, nanorod, nanotube or nanoparticle in each sensing element.

11. The device of claim 10, wherein:
more than two nanowires, nanorods, nanotubes nanoparticles or combinations thereof are implemented as an interconnected network in each sensing element; or,
the network is random or an aligned array of the nanowires, nanorods, nanotubes nanoparticles or combinations thereof.

12. The device of claim 1, wherein the transduction material is permeable to the target analyte.

13. The device of claim 1, wherein the dielectric substrates of every one of the sensing elements comprise different dielectric materials.

14. The device of claim 1, wherein the dielectric substrates of at least two of the sensing elements comprise the same dielectric material.

15. The device of claim 1, wherein the sensing elements comprise a resistor, a capacitor, a diode, a transistor, an electrochemical cell or a combination thereof.

16. The device of claim 15, wherein the resistor is a chemiresistor.

17. The device of claim 1, wherein the target analyte is a volatile organic compound, an amine, a C1-8 alkane, an air pollutant, a pesticide, a chemical warfare agent, a solvent, an industrial hazard, a disease marker, an alcohol, drug or a mixture thereof.

18. A process for sensing a target analyte in a gas, liquid or vapor sample, the process comprising:
exposing the device as defined in claim 1 to a gas, liquid or vapor sample containing a target analyte; and,
measuring a different sensing response between the at least two sensing elements according to one or more transduction modes.

19. The process of claim 18, wherein the sample is a vapor mixture comprising constituents of ambient air or breath, where at least one of the constituents acts as an interference to target analyte detection.

20. The process of claim 19, wherein the device is operated in transistor mode and one or more of threshold voltage, hysteresis, subthreshold slope or swing, hole and electron mobilities, ON and OFF currents and ON/OFF current ratio are computed and followed as a function of target analyte concentration to provide a measure of different interaction strengths of the device with the target analyte.

* * * * *